United States Patent [19]

Fischer

[11] Patent Number: 5,332,092
[45] Date of Patent: Jul. 26, 1994

[54] PROTECTIVE SYRINGE SHEATH AND METHOD OF USE

[75] Inventor: Dan E. Fischer, Sandy, Utah

[73] Assignee: Ultradent Products, Inc., South Jordan, Utah

[21] Appl. No.: 19,263

[22] Filed: Feb. 16, 1993

[51] Int. Cl.$^5$ .............................................. A61M 5/32
[52] U.S. Cl. ................................. 206/365; 206/305; 604/263
[58] Field of Search .................. 206/365, 305, 306, 69; 150/154; 604/192, 197, 198, 199, 263

[56] References Cited

U.S. PATENT DOCUMENTS

| | | | |
|---|---|---|---|
| 4,164,285 | 8/1979 | Dorman | 206/306 |
| 4,241,828 | 12/1980 | Bourdelle et al. | 206/69 |
| 4,757,381 | 7/1988 | Cooper et al. | 206/69 |
| 4,883,469 | 11/1989 | Glazier | 604/263 |
| 5,021,049 | 6/1991 | Howard | 206/365 |
| 5,061,246 | 10/1991 | Anapliotis | 604/263 |
| 5,116,326 | 5/1992 | Schmidt | 604/263 |
| 5,219,338 | 6/1993 | Haworth | 604/263 |

*Primary Examiner*—Paul T. Sewell
*Assistant Examiner*—Marie Denise Patterson

*Attorney, Agent, or Firm*—Workman Nydegger & Jensen

[57] ABSTRACT

A protective covering and method of use for preventing contamination of a syringe used to deliver material to a surface, so as to permit subsequent reuse of the syringe. The syringe comprises a barrel containing the material, a plunger for expelling the material from the barrel, and a removable delivery tip. The protective covering includes a collapsible sleeve for enclosing the syringe so as to provide a barrier to protect the syringe from contamination by an environment. A first and a second portion form the collapsible sleeve. The first portion has a width greater than the widest portion of the syringe. The second portion has a width smaller than the first portion which conforms to the width and length of the barrel so as to provide a snug fit around the barrel. An aperture is formed at the end of the collapsible sleeve through which a portion of the removable delivery tip passes when the syringe is inserted into the sleeve so that that portion of the tip is exposed to the outside environment. The collapsible sleeve may be heat sealed around the syringe. Once the syringe has been used, the syringe may be removed from the sleeve without being contaminated. The removable delivery tip is removed while the syringe is still enclosed within the sleeve.

10 Claims, 6 Drawing Sheets

PROTECTIVE SYRINGE SHEATH AND METHOD OF USE

BACKGROUND

1. Field of the Invention

The present invention relates to apparatus and methods for preventing contamination of a syringe used for delivering materials to surfaces so as to permit subsequent reuse of the syringe without cross contamination. More particularly, the present invention relates to protective coverings and methods for preventing contamination of dental syringes.

2. Background Art

Applying materials through syringes to teeth or mouth surfaces is an important process in common dental procedures. Generally, the syringes are used to express materials such as fillings, dental composites, bonding agents, or the like onto teeth surfaces.

During this process, the syringe can become contaminated as it comes into contact with a patient's mouth and/or from gloves worn by a practitioner. Often, not all of the material is used on a single patient. Because such materials are expensive, a common practice is to attempt to disinfect the syringe by wiping it down so it can be re-used. However, such efforts are not always completely effective, which leads to risk of cross contamination of infectious disease from one patient to another, if proper procedure is not followed by the practitioner.

Even when effective, such disinfecting procedures are time consuming. It would thus be preferable to simply discard the syringe after each use. However, the cost of materials makes this prohibitive from a cost point of view.

Small unit dose cartridges have been devised, but they are so small that they are very difficult to handle and control in the oral cavity with any real precision. Further, even the material in these cartridges is often not used entirely on a single patient. Thus, to date, these problems remain largely unsolved.

BRIEF SUMMARY AND OBJECTS OF THE INVENTION

The present invention seeks to resolve the above problems which have been experienced in the art. More particularly, the apparatus of this invention constitutes an advancement in preventing cross contamination and minimizing waste of materials in the dental or other related arts, as evidenced by the following objects and advantages realized by the invention over the prior art.

One object of the present invention is to provide a protective covering for syringes wherein the shape of the covering conforms to the shape of the syringe, thereby avoiding obstruction of sight of the user during use of the syringe within the protective covering.

Another important object of the present invention is to provide a protective covering for syringes wherein the shape of the covering is such that the control and feel of the user are not obstructed by excess material.

An additional important object of the present invention is to provide a protective covering for syringes wherein a passageway is provided for simple and smooth passage of a portion of the tip through the protective covering such that only that portion is exposed to the outside environment.

Still another important object of the present invention is to provide a protective covering for syringes which can be heat sealed at the opening so that any excess covering material may be removed with each use of the syringe, and all of the syringe except a portion of the delivery tip will thereby be completely enclosed within the protective covering, without danger of the protective covering sliding down and over the syringe, exposing the syringe to possible contamination.

A further important object of the present invention is to provide a protective covering for syringes which is formed such that insertion of a syringe into the covering is quick and simple.

Still another important object of the present invention is to provide a method for using the protective covering for syringes wherein only the removable tip of the syringe is contaminated, and the syringe can be removed from the protective covering while remaining uncontaminated.

Additional objects and advantages of the invention will be set forth in the description which follows, or in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention comprises a protective covering for enclosing and protecting the syringe from contamination during use.

The protective covering of the present invention comprises two portions. The first portion has a width which can accommodate the area of largest width of the syringe. Typically, this area on the syringe includes the finger wings which project outwardly from the main body of the syringe for use as a fingerhold for the user.

The protective covering may also comprise an enlarged insertion diameter for allowing quick and easy insertion of the syringe into the covering. In the preferred embodiment, a section of the protective covering thus flares outward to a diameter larger than the diameter of the first portion. Since this section is larger, it is easier to pull the sides of the covering apart and insert the syringe within.

The second portion of the protective covering has a width smaller than the width of the first portion and sized so as to snugly fit around the barrel of the syringe. The length of the second portion corresponds to the length of the barrel of the syringe. This second portion conforms to the shape of the syringe. The tip of this second portion of the protective covering tapers to a point. The portion tapers such that it conforms to the shape of the tip, thereby preventing the presence of excess covering material around the delivery tip, such that excess covering material around the barrel and tip of the syringe is avoided, thereby avoiding obstruction of sight of the user during use of the syringe while within the protective covering.

Another advantage to the protective covering being sized to conform to the shape and length of the syringe irrespective of how much material is left therein is that the feel and control of the user is not hampered by excess covering material bunching up within the hand of the user.

The protective covering of the present invention is preferably comprised of a thermoplastic material. Once the syringe is inserted within the protective covering, the excess covering material can be cut off and removed, while at the same time, sealing the ends of the protective covering to seal the syringe within the protective covering.

After use of the syringe, the end of the protective covering which has been heat sealed is then cut off, thus opening the protective covering. The covered syringe is grasped so as to touch only the outer portion of the protective covering. Using the fingers of this hand to manipulate the cover and pull it down and over the syringe, the syringe is uncovered. The uncontaminated syringe is then grasped with a clean, gloved hand and is pulled out, being careful that the syringe does not touch the contaminated outer portion of the protective covering.

Before the protective covering is completely removed from the syringe, the delivery tip of the syringe is grasped through the protective covering and removed from the syringe. The removed delivery tip remains within the protective covering and is discarded therewith. The uncontaminated syringe can be attached to a new delivery tip, placed in a new protective covering and then reused without fear of causing cross-contamination.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

A. The Protective Covering

Figure 1:
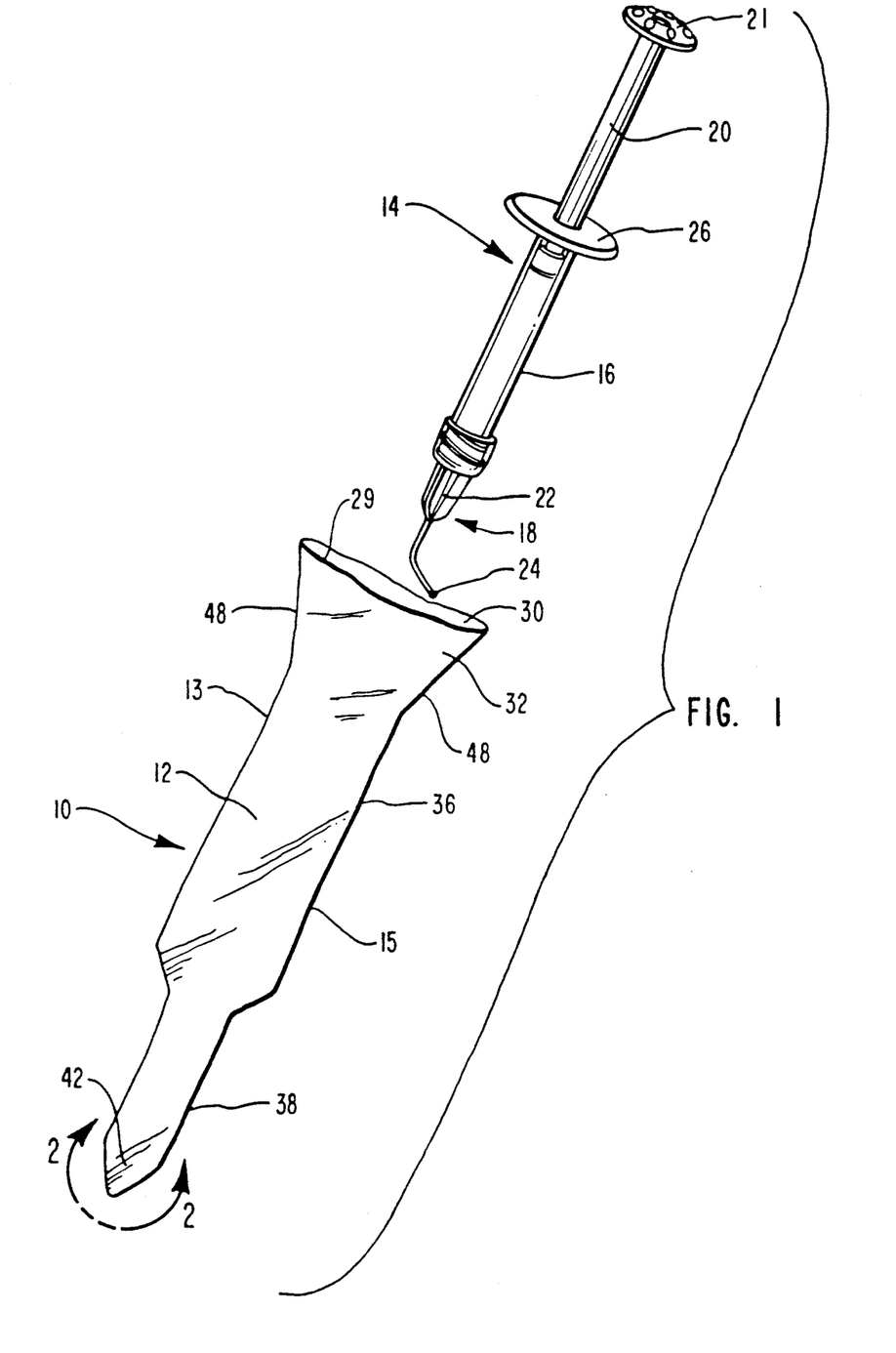
FIG. 1 is a perspective view of the presently preferred embodiment of the protective covering of the present invention showing a syringe about to be inserted therein.

Reference is now made to the drawings wherein like parts are designated with like numerals throughout. Referring first to FIG. 1, one presently preferred embodiment of the present invention is illustrated and generally designated 10.

In one aspect of the invention, protective covering 10 comprising a covering means for enclosing a syringe so as to provide a barrier to protect the syringe from contamination by an environment. The covering means allows the syringe to be used within a contaminated environment and then reused without fear of cross-contamination. By covering the syringe, the syringe need not be disinfected, and yet need not be thrown away after every use, so that material not used for one patient can still be reused for another, thus reducing waste and cost, while still assuring that there will be no cross contamination.

In the presently preferred embodiment, the covering means is comprises, for example, a collapsible sleeve 12 into which a syringe 14 may be inserted. Sleeve 12 is preferably made by sealing two pieces of thin, flexible plastic material at edges 13 and 15 around the periphery of sleeve 12, except across the opening 29. Once the syringe 14 is inside the collapsible sleeve 12, syringe 14 is protected from the outside environment.

Although other types of syringes may be used with the protective covering of the present invention, a syringe having a removable tip will be described as the syringe presently preferred to be used with the protective covering. As shown in FIG. 1, syringe 14 is to be inserted into the protective covering. Syringe 14 includes a barrel 16 filled with a material to be expressed, and a delivery tip 18. A plunger 20 enters barrel 16 longitudinally and presses against the material therein causing it to flow out of barrel 16 and through delivery tip 18.

In syringe 14, delivery tip 18 is removable. The delivery tip 18 is affixed to barrel 16 through some type of coupling such as a female luer-lock coupling, a screw fit coupling, a press-fit coupling, or other suitable coupling mechanism. The delivery tip is comprised of two portions, a connecting portion 22 which is coupled to barrel 16, and an extruding portion 24 through which the material is passed from the syringe. At the end of the barrel opposite delivery tip 18 is a pair of finger wings 26 projecting outwardly from the barrel.

Collapsible sleeve 12 is comprised of an inner surface 30 which contacts syringe 14 when syringe 14 is inserted into the covering 12, and an outer surface 32 with which syringe 14 does not come into contact when the syringe 14 is inserted into covering 12. When syringe 14 is used in dental procedures, outer surface 32 comes into direct contact with areas of contamination. Inner surface 30 remains uncontaminated. Therefore, the syringe 14, coming into contact only with inner portion 30, also remains uncontaminated.

Collapsible sleeve 12 is further comprised of a first portion 36 through which the syringe can be inserted, and a second portion 38, within which the barrel of the syringe is positioned. First portion 36 has a width larger than the finger wings 26 of syringe 14, which is typically the largest diameter of syringe 14. The syringe is comfortably accommodated, but without a large amount of excess covering material remaining around the syringe when the syringe is inserted into the collapsible sleeve 12.

Second portion 38 has a width smaller than the width of the first portion 36. Second portion 38 is sized so as to snugly fit around barrel 16 of the syringe 14, and has a length corresponding to the length of barrel 16. Therefore, second portion 38 conforms to the shape of the barrel 16 and excess covering material around the barrel 16 of the syringe 14 is minimized.

This lack of excess covering material around the barrel is an important advantage of the present invention. When there is a quantity of excess covering material around the barrel of the syringe, the sight of the user may be obstructed, and the control and feel of the syringe when using it may be hampered. When the sleeve 12 conforms to the shape of the syringe, these problems are minimized.

As seen in FIG. 1, the second portion 38 may comprise a tip receiving means for providing an area of narrow diameter for receiving the tip 18 of syringe 14 and allowing passage of the extruding portion 24 of tip 18 through collapsible sleeve 12 such that extruding portion 24 is exposed to an outside environment while the remainder of the syringe is enclosed within collapsible sleeve 12.

In the preferred embodiment, the tip receiving means comprises a narrowed portion 42 (see FIG. 2) located at one end of second portion 38. Narrowed portion 42, as can be seen in exploded view in FIG. 2, tapers to a point wherein an aperture 44 is located. When syringe 14 is positioned within collapsible sleeve 12, connecting portion 22 of tip 18 is fit snugly within narrowed portion 42 and extruding portion 24 of tip 18 which passes through aperture 44 into the outside environment. Aperture 44 is sized so as to accept extruding portion 24, yet not allow any contamination to pass from the outside environment to the uncontaminated environment within protective collapsible sleeve 12.

Figures 2, 3:
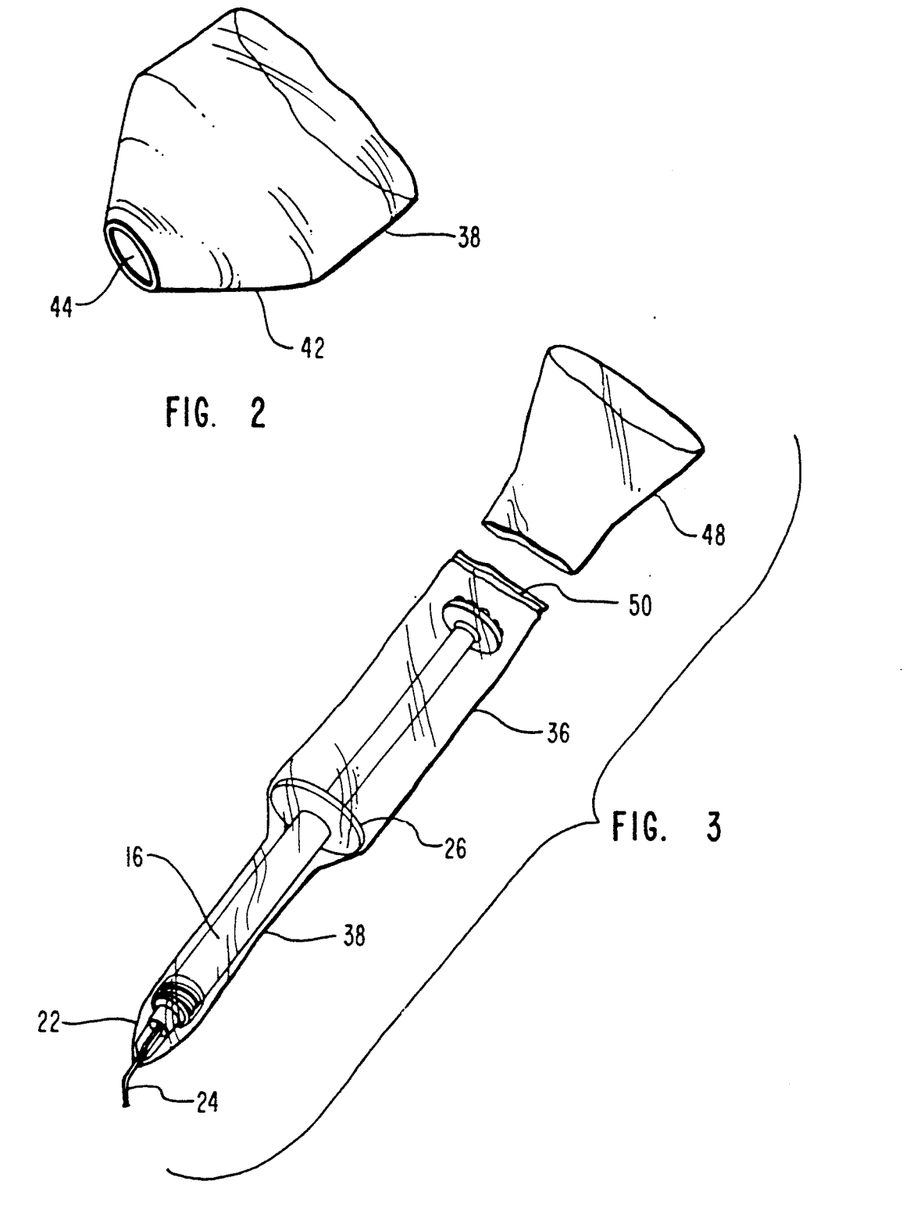
FIG. 2 is an enlarged perspective view taken around line 2—2 of FIG. 1, illustrating the aperture through which the extruding portion of the tip of the syringe is passed.
FIG. 3 is a perspective view of the presently preferred embodiment of the protective covering of the present invention wherein the end is heat sealed and the excess portion is cut off after the syringe has been inserted therein.

One advantage of aperture 44 is that the syringe can be quickly and easily slipped into the covering 12 and is then ready for use. Alternatively, aperture 44 may also be provided by using the tip 24 of the syringe to puncture the covering 12 by thrusting the tip 24 against the bottom and poking a hole therethrough.

In order to allow quick and simple insertion of syringe 14 into collapsible sleeve 12, first portion 36 may be further comprised of an inserting means for providing a first enlarged insertion diameter. As can be seen in the preferred embodiment illustrated in FIGS. 1 and 3, the inserting means may comprise, for example, a flared portion 48 which flares outward to a diameter larger than the diameter of the first portion 36. With the larger diameter of flared portion 48, the action of opening collapsible sleeve 12 in order to insert syringe 14 is made easier and less clumsy.

In the presently preferred embodiment, the collapsible sleeve 12 is comprised of a thermoplastic material capable of being heat-sealed. As can be seen in FIG. 3, once the syringe in inserted within the covering 12, the excess material can be cut off and removed. The ends of the protective covering can then be heat sealed as shown at 50 so as to seal the syringe into the covering 12. Once sealed, the syringe is prevented from becoming contaminated. Heat sealing machines known in the art can be used to simultaneously seal the end and cut off the excess portion.

Another advantage of being able to heat seal the collapsible sleeve is that the heat seal is used as a lock to keep the sleeve from sliding down and off the syringe. Furthermore, as noted above, excess material causes obstruction of vision and interferes with the control and feel of the user. With the excess portion cut off, the obstruction and interference with feel are minimized.

Method of Use of the Protective Covering

FIGS. 3-7 best illustrate the novel method of using the protective covering of the present invention to prevent contamination of a syringe so as to permit subsequent reuse of the syringe. The method comprises the steps of initially obtaining a protective covering as described above, grasping the flared end 48 of the first portion 36 of the covering 12, opening the covering means, and inserting the syringe into the protective covering 12 so that the extruding portion or tip 24 has passed through aperture 44 so as to be in contact with the outside environment, while the remainder of the syringe remains enclosed within the protective covering 12.

The next step of the method comprises cutting away any excess of the protective cover 12 which extends past the end of the syringe, and then heat sealing the end 50 of the protective covering 12 so as to seal the syringe within the protective covering 12.

Figure 4:
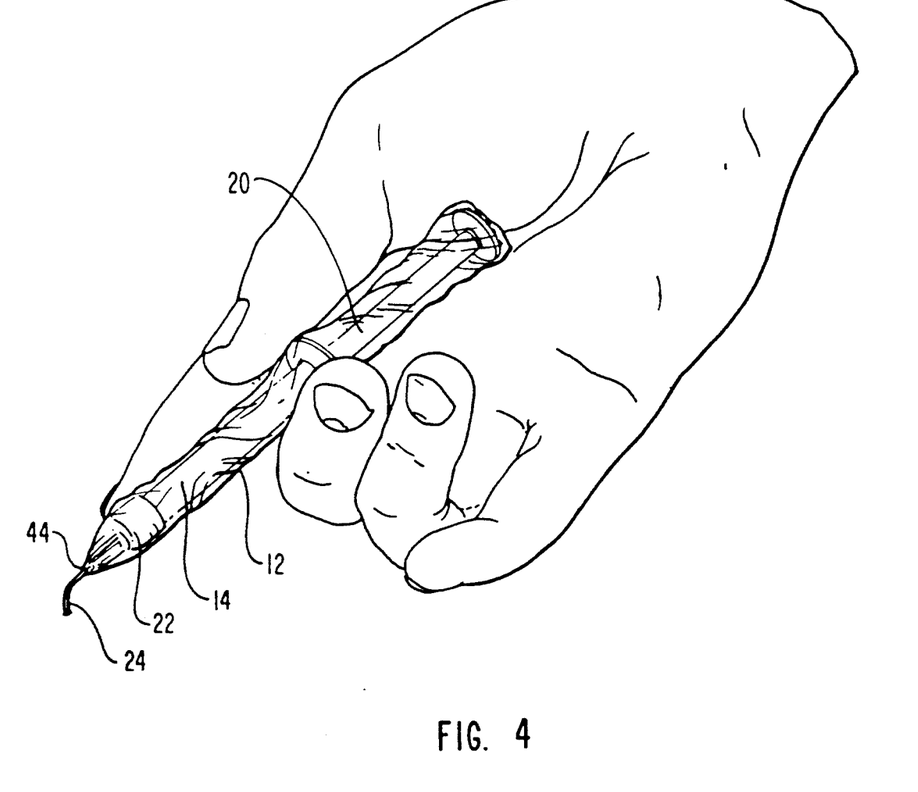
FIG. 4 illustrates a syringe positioned within the protective cover of the present invention as held in the hand of a user, ready for use.

Now the syringe may be used to express material onto a surface. While within the protective covering 12, the plunger 20 of the syringe may still be easily pushed down. Preferably, the syringe is held in the hand as shown in FIG. 4. The end or head 21 of the plunger 20 is held against the fleshy portion of the palm, while the barrel 16 is held within the fingers and thumb. By this method of holding the syringe, the user can use his or her fingers to directly guide the positioning of the syringe, while the palm of the hand is used to push the plunger 20 and expel the material.

Figure 5:
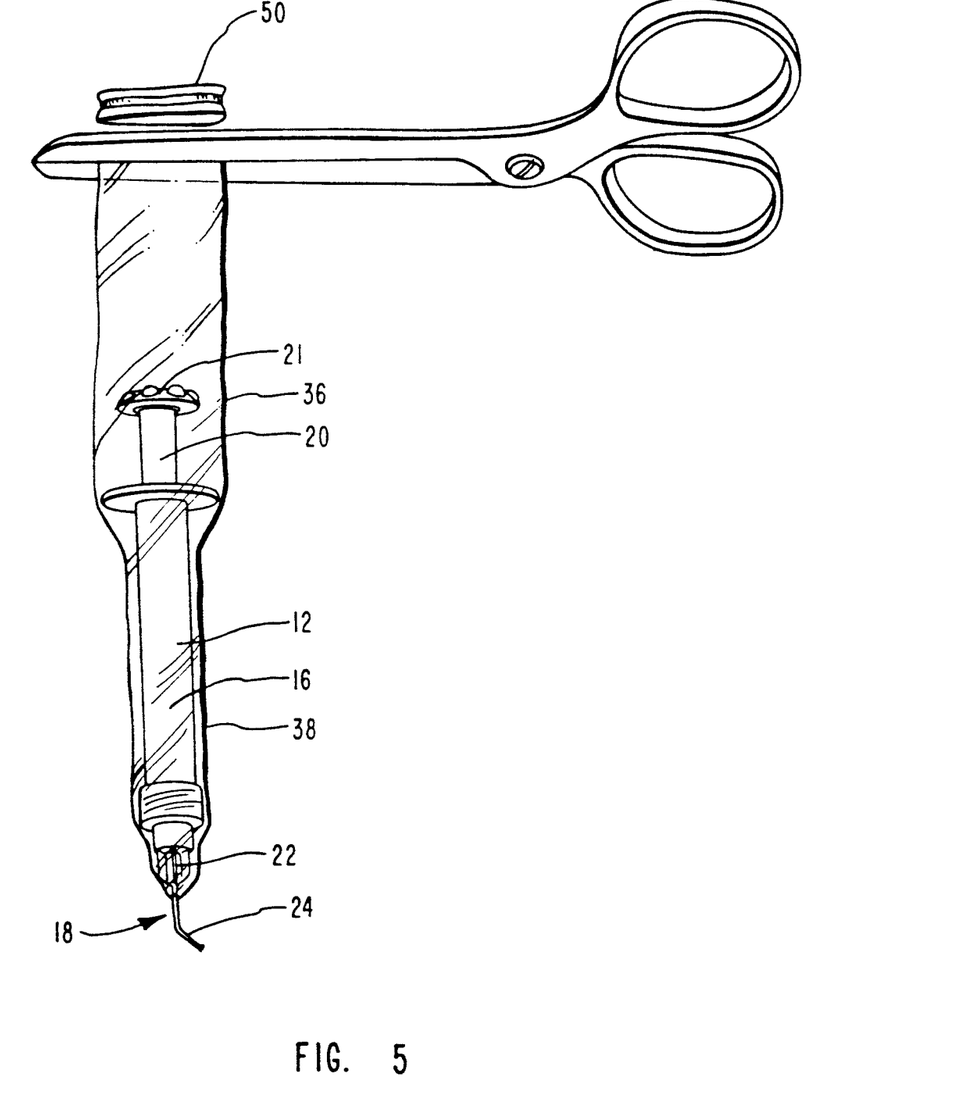
FIG. 5 illustrates the step of cutting the heat sealed portion off the protective covering after the syringe has been used.

Once the user is finished with the syringe, the end 50 of the protective covering 12 which has been heat sealed is then cut off near the end 21 of plunger 20, thus opening the end of the protective covering 12. FIG. 5 illustrates this step.

Figure 6:
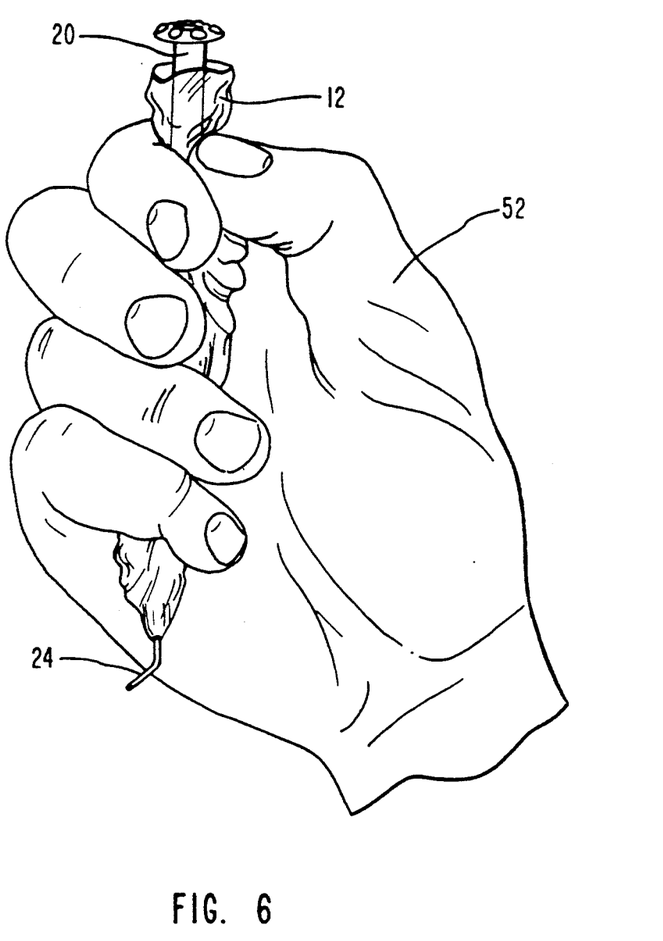
FIG. 6 illustrates the step of removing the syringe from the protective covering using one hand so as to keep the second hand uncontaminated for contact with the uncontaminated syringe.
Figure 7:
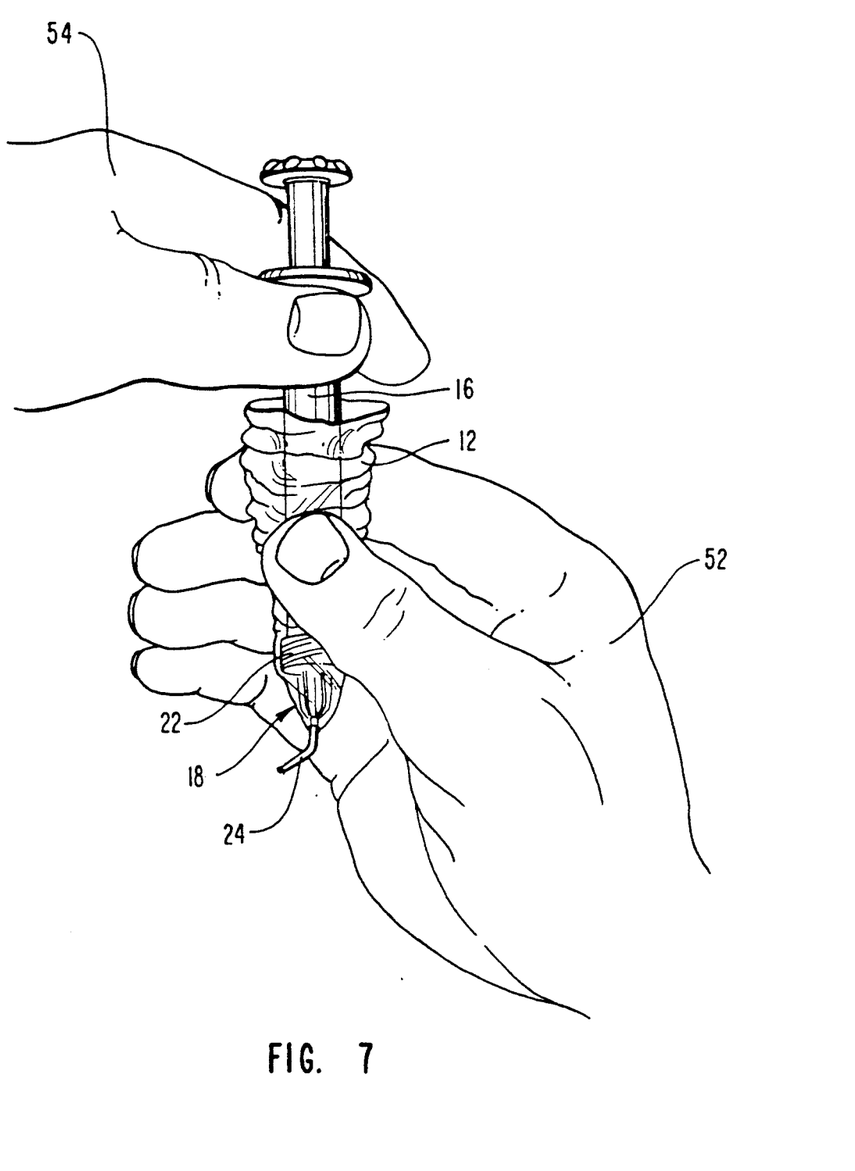
FIG. 7 illustrates the step of removing the uncontaminated syringe with an uncontaminated hand while removing the contaminated tip from the syringe without the syringe touching the outer, contaminated portion of the protective covering.

Next, as shown in FIG. 6, a first hand 52 is used to pull the protective cover 12 down and over the syringe while leaving the other hand 54 free and uncontaminated. When the protective covering 12 is pulled down far enough to allow the syringe to be removed without the syringe touching the outer portion of the protective covering 12, the second, uncontaminated hand 55 is used to grasp the barrel 16 and pull the syringe out, as shown in FIG. 7.

Before the syringe is completely removed, and while the tip 18 of the syringe is still within the protective covering 12, the tip 18 is grasped through covering 12 and is twisted by the first hand 52 and removed from the syringe. This step is performed while the second, uncontaminated hand 54 is holding the syringe barrel 16. The removed tip 18 remains inside the protective cover 12 as the syringe is pulled out by the second, uncontaminated hand 54. FIG. 7 illustrates this step. The hand 52 which held the outside of the protective covering 12 is shown twisting the tip 18 of the 16 syringe while the clean hand 54 is holding the syringe barrel 16.

Only the non-contaminated inside of the protective covering 12 ever touches the syringe. This leaves the syringe free from contamination and reusable.

C. Summary

The protective covering and method for use of the protective covering prevent a syringe from being contaminated with each use. The covering is conformed to the shape of the syringe so that excess covering material does not block the vision or hamper the control and feel of the syringe when used. Only the removable tip is disposed of between each use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A protective covering in combination with a syringe having a removable tip, a barrel in which material to be extruded is housed, and a plunger in communication with the barrel for pushing the material to be extruded through the barrel, the removable tip having a connecting portion removably connecting the tip to the syringe and an extruding portion through which material is extruded from the syringe, the protective covering comprising two thin, flexible sheets bonded at the edges thereof so as to form an essentially flat, collapsible sleeve of thermoplastic material that is heat sealable and that together form a covering means for enclosing the entire syringe except for the extruding portion of the removable tip so as to provide a barrier to protect the entire syringe except for the extruding portion of the removable tip from contamination by an environment, said covering means comprising:
   an inner surface which contacts the syringe when the syringe is inserted into said covering means;
   an outer surface with which the syringe does not come into contact when the syringe is inserted into said covering means;
   a first portion through which the syringe can be inserted, said first portion having a width greater than the widest section of the syringe;
   a second portion having a width smaller than the width of said first portion and sized so as to snugly fit around the barrel of the syringe, and having a length corresponding to the length of the barrel of the syringe, said second portion conforming to the shape of the barrel such that excess material around the barrel and tip of the syringe is minimized; and
   tip receiving means positioned on said second portion of said covering means for receiving the tip of the syringe and for allowing passage of the extruding portion of the tip of the syringe through said covering means into an outside environment such that the extruding portion of the tip of the syringe is exposed to the outside environment while the remainder of the syringe is enclosed with said covering means.

2. A protective covering as defined in claim 1, wherein the covering means comprises a thermoplastic material.

3. A protective covering as defined in claim 1, wherein the first portion further comprises insertion means for providing an enlarged insertion diameter for allowing quick and simple insertion of the syringe into said covering means.

4. A protective covering as defined in claim 1, wherein said tip receiving means comprises an aperture positioned such that when the syringe is placed within said covering means, the extruding portion of the tip passes through said aperture while the connecting portion of the tip and the remainder of the syringe remain within said covering means.

5. A protective covering as defined in claim 4, wherein said tip receiving means comprises a portion which tapers to a point so as to generally conform to the shape of the tip of the syringe, the point to which the receiving means tapers being the aperture through which the extruding portion of the tip of the syringe passes when the syringe is inserted into the covering means.

6. A protective covering in combination with a syringe having a removable tip, a barrel in which material to be extruded is housed, and a plunger in communication with the barrel for pushing the material to be extruded through the barrel, the removable tip having a connecting portion removably connecting the tip to the syringe and an extruding portion through which material is extruded from the syringe, the protective covering comprising two thin, flexible sheets bonded at the edges thereof so as to form an essentially flat, collapsible sleeve of thermoplastic material that is heat sealable and that together form a covering means for enclosing the entire syringe except for the extruding portion of the removable tip so as to provide a barrier to protect the entire syringe except for the extruding portion of the removable tip from contamination by an environment, said covering means comprising:
   an inner surface which contacts the syringe when the syringe is inserted into said covering means;
   an outer surface with which the syringe does not come into contact when the syringe is inserted into said covering means;
   a first portion through which the syringe is inserted, the first portion having a width greater than the widest section of the syringe, and further comprising insertion means positioned on an end of said covering means providing a first enlarged insertion diameter for allowing quick and simple insertion of said syringe into said covering means; and
   a second portion having a width smaller than the width of the first portion and sized so as to snugly fit around the barrel of the syringe, and having a length corresponding to the length of the barrel of the syringe, said second portion conforming to the shape of the barrel such that exceeds material around the barrel and tip of the syringe is minimized; and
   tip receiving means positioned on said second portion of said covering means for providing a second reduced diameter for receiving the tip of the syringe and allowing passage of the extruding portion of the tip of the syringe through said covering means such that the extruding portion of the tip of the syringe is exposed to an outside environment while the remainder of the syringe is enclosed within said covering means.

7. A protective covering as defined in claim 6, wherein said tip receiving means comprises an aperture positioned such that when the syringe is placed within said covering means, the extruding portion of the tip passes through said aperture while the connecting portion of the tip and the remainder of the syringe remain within said covering means.

8. A protective covering as defined in claim 7, wherein said tip receiving means comprises a portion which tapers to a point so as to conform to the shape of the tip of the syringe, the point to which the receiving means tapers being the aperture through which the extruding portion of the tip of the syringe passes when the syringe is inserted into the covering means.

9. A protective covering as defined in claim 8, wherein the covering means comprises a thermoplastic material.

10. A protective covering in combination with a syringe having a removable tip, a barrel in which material to be extruded is housed, and a plunger in communication with the barrel for pushing the material to be extruded through the barrel, the removable tip having a connecting portion removably connecting the tip to the syringe and an extruding portion through which material is extruded from the syringe, the protective covering comprising two thin, flexible sheets bonded at the edges thereof so as to form an essentially flat, collapsible sleeve made of a thermoplastic material into which the syringe may be inserted, said collapsible sleeve comprising:

an inner surface which contacts the syringe when the syringe is inserted into the covering means;

an outer surface with which the syringe does not come into contact when the syringe is inserted into said covering means;

a first portion through which the syringe is inserted, the first portion having a width greater than the widest section of the syringe; and a second portion having a width smaller than the width of the first portion and sized so as to snugly fit around the barrel of the syringe, and having a length corresponding to the length of the barrel of the syringe, said second portion conforming to the shape of the barrel such that excess material around the barrel and tip of the syringe is minimized; and said first portion further comprising an end which flares outward to an enlarged diameter for allowing quick and simple insertion of said syringe into said collapsible sleeve, and said second portion further comprising an end tapering to an aperture therein, through which the extruding portion of the tip of the syringe is passed such that the extruding portion of the tip of the syringe is exposed to an outside environment while the remainder of the syringe is enclosed within said collapsible sleeve.

* * * * *

UNITED STATES PATENT AND TRADEMARK OFFICE
CERTIFICATE OF CORRECTION

PATENT NO.  : 5,332,092
DATED       : July 26, 1994
INVENTOR(S) : DAN E. FISCHER It is certified that error appears in the above-indentified patent and that said Letters Patent is hereby corrected as shown below:

Column 4, line 11, "comprising" should be --comprises--
    Column 4, line 23, delete "is"
    Column 6, line 64, delete "16"
    Column 8, line 50, "exceeds" should be --excess--

Signed and Sealed this

Twenty-first Day of February, 1995

Attest:

BRUCE LEHMAN

Attesting Officer    Commissioner of Patents and Trademarks